United States Patent
Naclerio

(10) Patent No.: US 9,440,087 B2
(45) Date of Patent: Sep. 13, 2016

(54) AED WITH ALTERNATE SHOCK SWITCH

(75) Inventor: Edward J. Naclerio, Madison, CT (US)

(73) Assignee: DEFIBTECH, L.L.C., Guilford, CT (US)

( * ) Notice: Subject to any disclaimer, the term of this patent is extended or adjusted under 35 U.S.C. 154(b) by 577 days.

(21) Appl. No.: 12/928,319

(22) Filed: Dec. 8, 2010

(65) Prior Publication Data

US 2012/0150246 A1    Jun. 14, 2012

(51) Int. Cl.
*A61N 1/39* (2006.01)

(52) U.S. Cl.
CPC ........... *A61N 1/3931* (2013.01); *A61N 1/3968* (2013.01); *A61N 1/3993* (2013.01)

(58) Field of Classification Search
CPC ............... A61N 1/39; A61N 1/3912
USPC .......................................... 607/5–8, 115, 142
See application file for complete search history.

(56) References Cited

U.S. PATENT DOCUMENTS 5,797,969 A * 8/1998 Olson et al. ................... 607/5

* cited by examiner

*Primary Examiner* — Christopher D Koharski
*Assistant Examiner* — Michael D Abreu
(74) *Attorney, Agent, or Firm* — William B. Gowanlock

(57) ABSTRACT

A semi-automated AED with a second shock switch. In an illustrative embodiment, programming running on the AED after prompting a user of the AED to push a shock switch looks to see if an event associated with pushing the shock switch, such as the delivery of a shock, has occurred. If the event being monitored for has not occurred within a given time, the user is prompted to push another button to initiate the event.

3 Claims, 5 Drawing Sheets

AED WITH ALTERNATE SHOCK SWITCH

TECHNICAL FIELD

The present invention relates to automated external defibrillators, and, more specifically, to a alternate system to initiate a shock to a victim.

BACKGROUND OF THE INVENTION

External defibrillators are emergency medical devices designed to supply a controlled electric shock (i.e., therapy) to a person's (e.g., victim's) heart during cardiac arrest. This electric shock is delivered via pads that are electrically connected with the external defibrillator and in contact with the person's body.

To provide a timelier rescue attempt for a person experiencing cardiac arrest, some external defibrillators have been made portable, by utilizing battery power (or other self-contained power supplies). In addition, many portable external defibrillators have programming to make medical decisions making possible operation by non-medical personnel.

These portable external defibrillators, commonly known as automated external defibrillators (AEDs), including automatic and semi-automatic types, have gained acceptance by those outside the medical profession and have been deployed in myriad locations outside of traditional medical settings. Due to the life saving benefits of AEDs, more and more non-medical users are purchasing and deploying AEDs in their respective environments. This allows for a rescue attempt without the delay associated with bringing the person to a medical facility, or bringing a medical facility to the person (e.g., a life support ambulance).

To assure the availability of an AED for use in a rescue, the functionality of AEDs is constantly assessed. Generally, AEDs having programming that conducts autonomous self-testing, and alerts a user to a problem. These self-tests focus on testing those aspects of the AED which can be tested, such as circuit continuity and circuit functionality.

Autonomous self-tests, however, cannot test every aspect of an AED. More precisely, some functions of an AED are actuated manually by a user. For example, in a semi-automatic AED, the shock switch, which is generally a contact switch, is depressed by a user to deliver a shock. The switch, which can function in many ways such as directly closing the shock circuit or activating a program to close the shock circuit, cannot be tested by the autonomous self-tests. As a result, any damage to the switch would not be detected until a manual interaction occurs, such as during a rescue when a user presses the button.

What is needed in the art is a alternate feature that can be used when a manually activated systems fails. Using the semi-automatic AED example discussed above as an example, a alternate system for the shock switch would be desirable.

Furthermore, other desirable features and characteristics of the present invention will become apparent for the subsequent detailed description of the invention and the appended claims, taken in conjunction with the accompanying drawings and this background of the invention.

SUMMARY OF THE INVENTION

The invention is a program for insertion into the customary programming of a device that has a manual mechanical interface used to precipitate an event. More precisely, the program looks to see if a user of the device has been prompted in a way that requires the user to interact with the manual mechanical interface. Then, the program looks for an outcome associated with the use of the manual mechanical interface. In the event the outcome associated with the manual mechanical interface is not detected, an alternate manual mechanical interface is identified that when interacted with will precipitate the event.

In one embodiment, a semi-automated AED (one which has a shock switch) has the program inserted into the regular AED programming. In this illustrative embodiment, the programming after prompting a user of the AED to push a shock switch looks to see if an event associated with pushing the shock switch, such as the delivery of a shock, has occurred. If the event being monitored for has not occurred within a given time, the user is prompted to push another button to initiate the event.

Other features, attainments, and advantages will become apparent to those skilled in the art upon a reading of the description when taken in conjunction with the accompanying drawings.

DETAILED DESCRIPTION OF EXEMPLARY EMBODIMENTS

Figure 1:
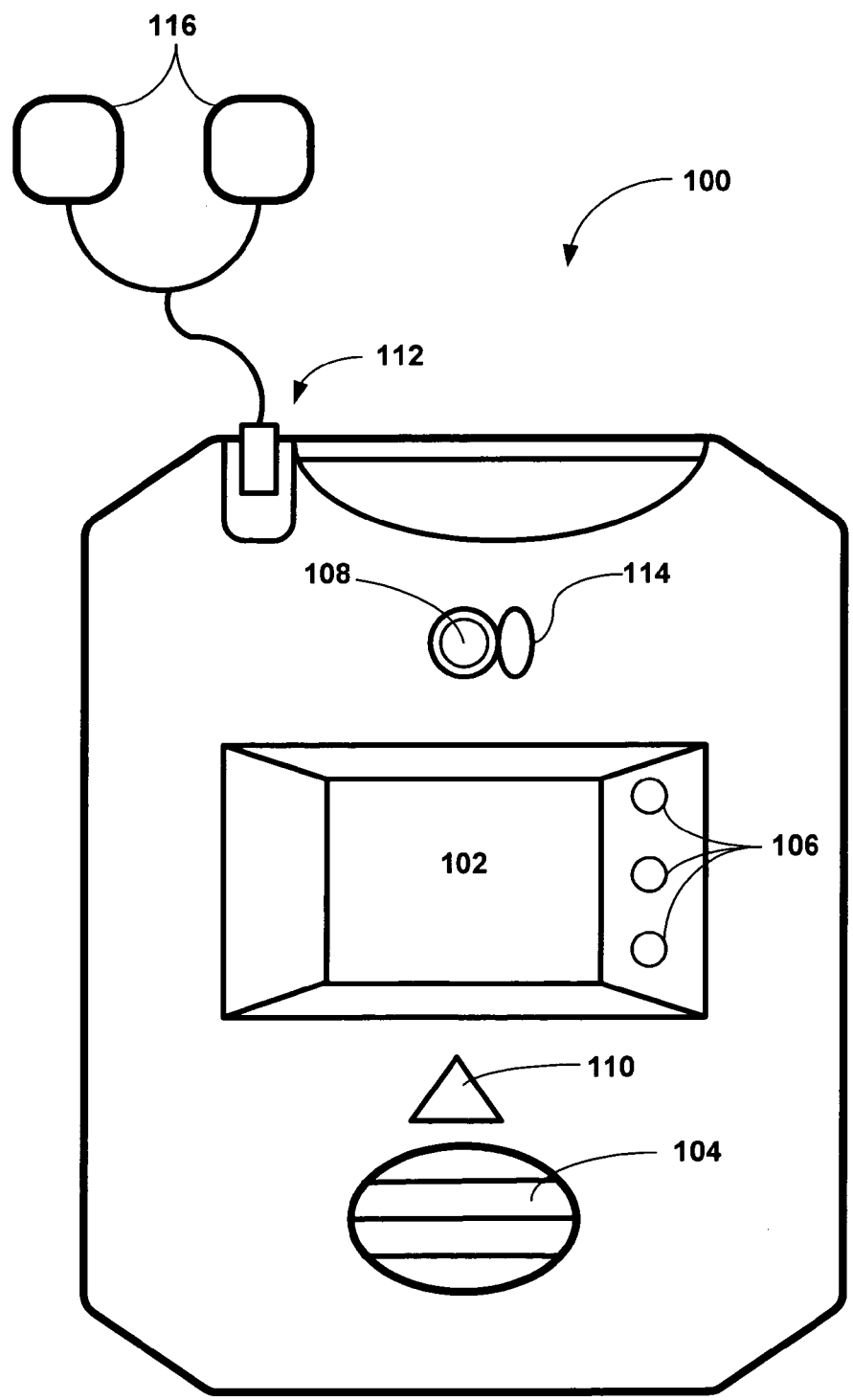
FIG. 1 is a top view of an illustrative AED on which the present invention may be used.

Turning now to the drawings, FIG. 1 illustrates a plan view of an AED unit 100. As seen in this FIG. 1, the AED unit 100 has a video display 102, a speaker 104 and a user interface 106. The AED unit 100 further includes an ON/OFF switch 108, a shock switch 110, a pad connector 112, and an active status indicator 114 (ASI) (e.g., a light source which blinks green indicating the unit is OFF but ready to operate normally, solid green indicating the unit is ON and operating normally, solid red indicating the unit is ON but having a problem, and blinking red indicating the unit is OFF but having a problem. If the ASI is not blinking, the unit is out of service). The pad connector 112 connects pads 116 to the AED unit 100.

Figure 2:
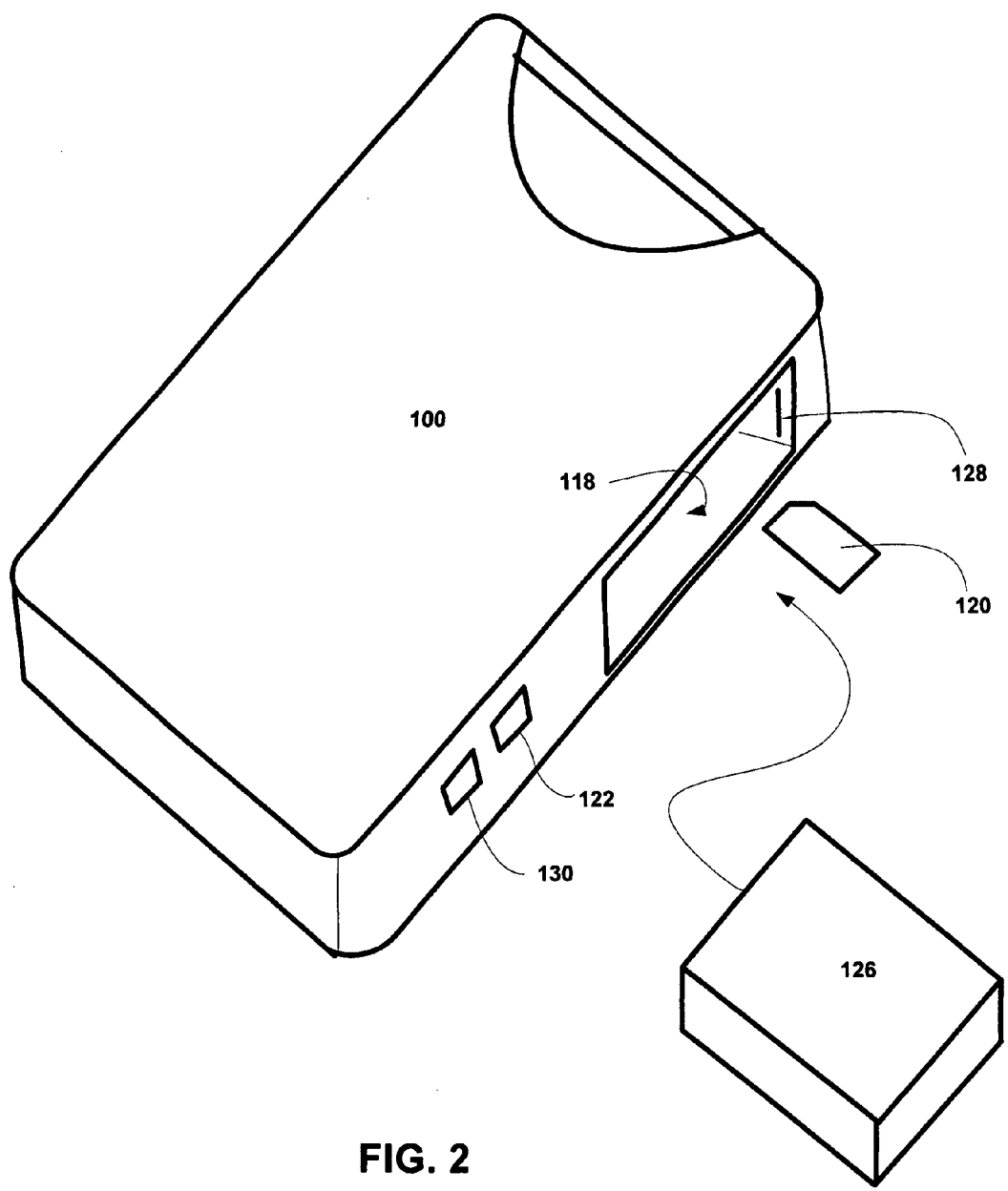
FIG. 2 is a perspective side view of the AED depicted in FIG. 1.
Figure 3:
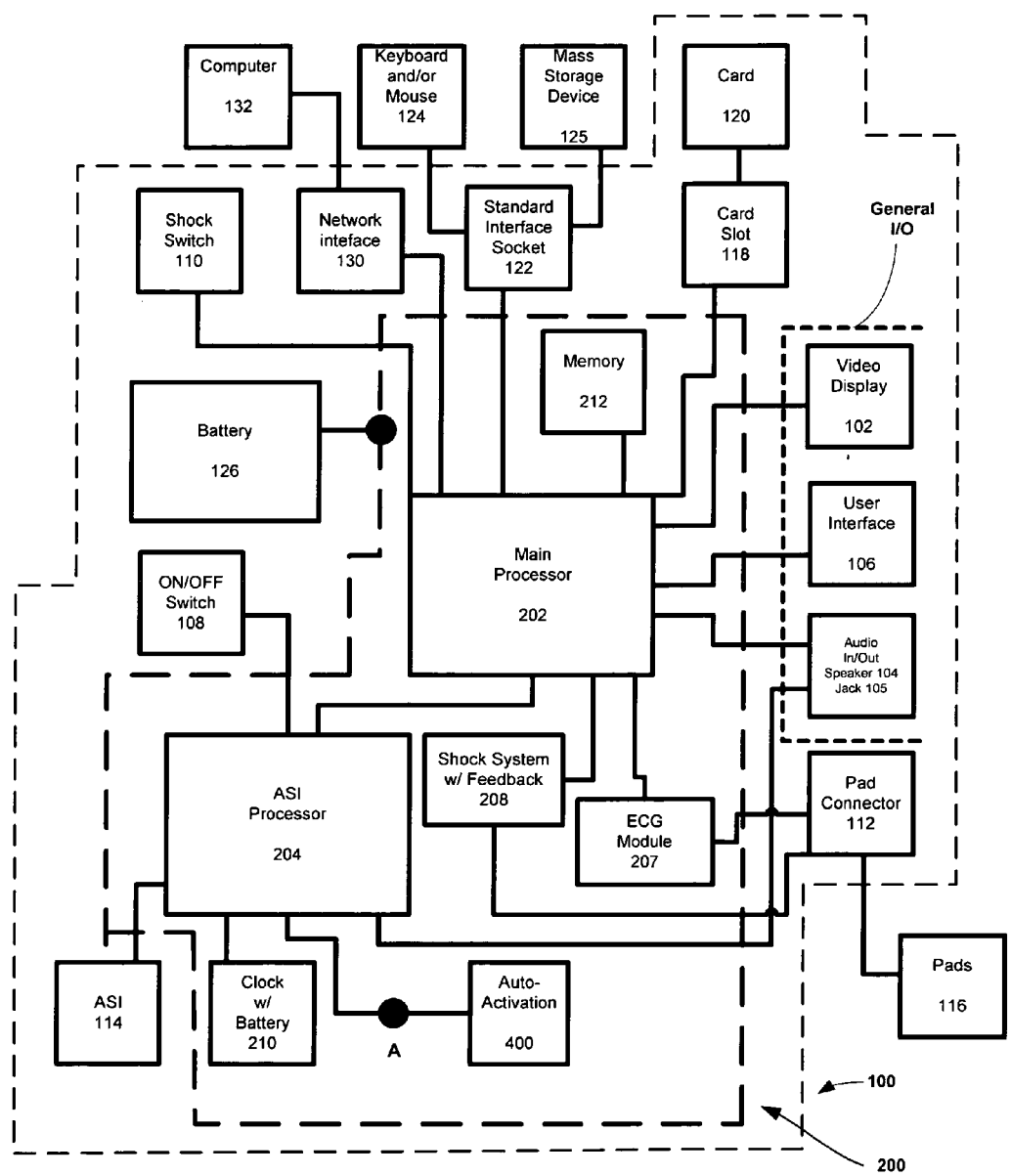
FIG. 3 is a functional block diagram of the components of the AED depicted in FIGS. 1 and 2.

Referring to FIG. 2, the AED unit 100 further includes a card port 118 for providing an electronic interface for a memory card 120 for data collection, a standardized interface socket 122, e.g., universal serial bus (more commonly known as a USB port) for connecting such items as a keyboard and/or mouse 124 or a mass storage device 125 (see FIG. 3), and a network interface 130 for connecting, for example a computer 132 (see FIG. 3). Further, the AED unit 100 has a pad slot 133 for storing the pads 116 when not in use.

The AED unit 100 includes a battery pack 126 that provides the main power. As illustrated, the battery pack 126 slides into a battery slot 128, but it could be an internal battery pack. Where the battery 126 is removably secured in the battery slot 128, a faulty battery can generally be replaced by a user.

FIG. 3 is a functional block diagram of an exemplary AED unit 100. The AED unit 100 includes at a minimum a computer programmed and running the necessary programming to conduct a rescue, such as ECG monitoring and patient defibrillation. While other programming could be provided, typical additional customary programming could include self-testing, including autonomous self-testing, and reporting of self-test results. Circuitry and programming of AED units is well known in the art.

The AED unit 100 typically has many operating modes, with some being sub-modes of primary modes. There are two primary modes—OFF and ON. The AED unit, from the user's perspective, is ON when the user activates the AED unit to perform a rescue. The AED unit, from the user's perspective, is OFF when the unit is not ON.

The OFF mode has several sub-modes including SELF-TEST and AUXILIARY. The OFF-SELF-TEST sub-mode is the default mode, as generally there is no true OFF (i.e., no power to the unit). More specifically, the AED unit when perceived OFF by a user is in the OFF SELF-TEST sub-mode.

In the OFF SELF-TEST sub-mode, the circuitry 200 of the AED unit 100 utilizes minimal power to maintain basic functions of the AED such as running a clock 210 (which is shown as having a alternate battery) and autonomously (i.e., without human intervention) initiating and running self-tests. Scheduled self-tests are generally initiated in response to the passage of time, and may vary is scope based on frequency. For example, self-tests may be daily, weekly, monthly and quarterly, with self-test occurring less frequently having greater scope. For example, daily self-tests could test limited portions of the circuitry while quarterly tests could fully test the shock circuit, with the others somewhere in between. The results of the last self-test in this illustrative AED 100 are displayed by an active status indicator 114, over which the AED programming has autonomous control.

For a rescue attempt, the AED unit 100 is put into the ON mode from the OFF SELF-TEST sub-mode by operation of the ON/OFF switch 108. After the rescue attempt, the AED unit 100 may be put back into the OFF SELF-TEST sub-mode by operation of the ON/OFF switch 108, or the programming may automatically put the AED unit into the OFF SELF-TEST sub-mode.

Figure 4:
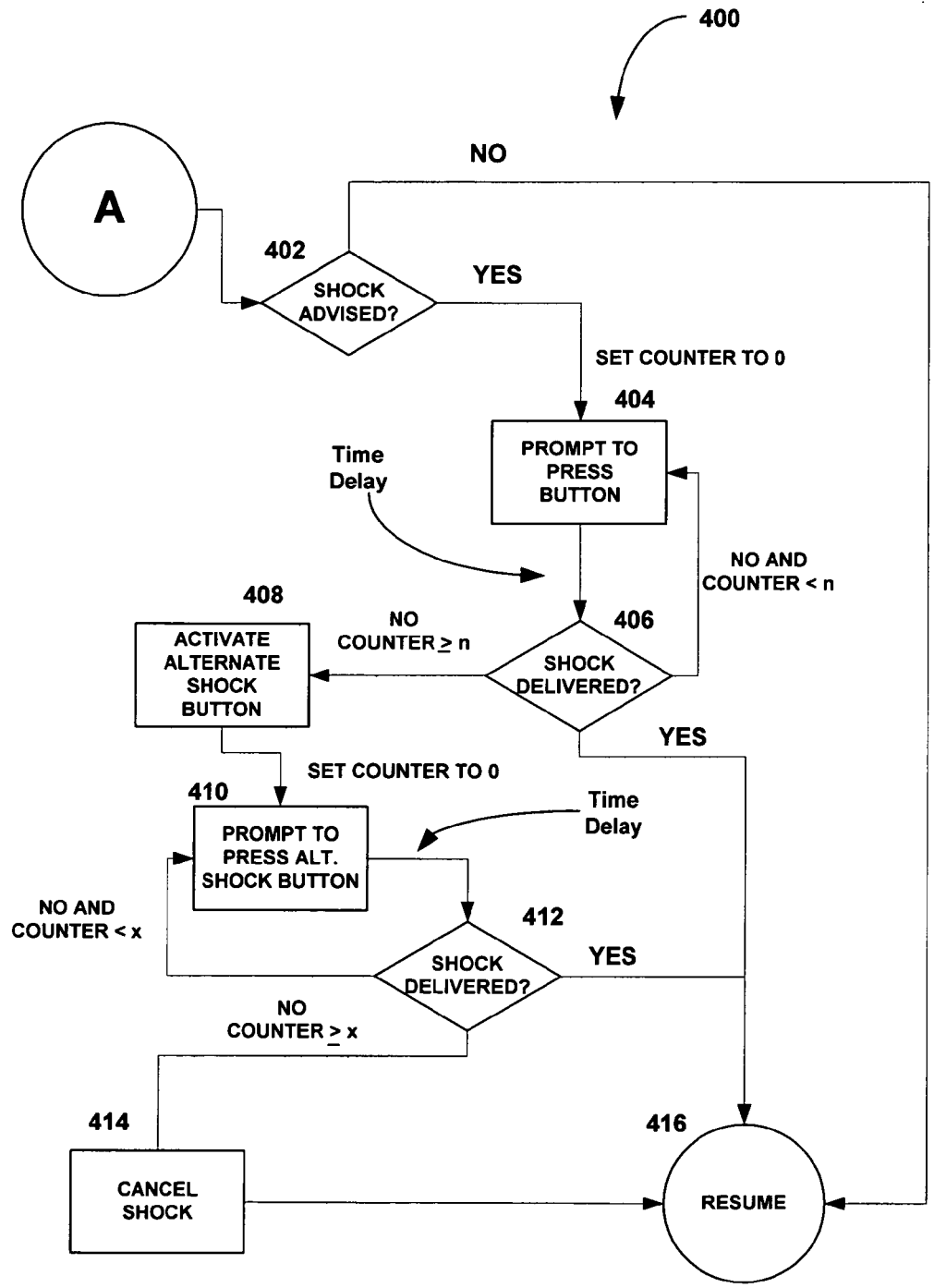
FIG. 4 is a block diagram of an embodiment of a computer program of the present invention.

Continuing with FIG. 4, FIG. 4 is a logic diagram (generally referred to by reference number 400) of the program inserted into the program code associated with a rescue attempt. In this illustrative embodiment, the AED unit is of the semi-automatic type; thus, it requires a manual action, a push of the shock switch, to provide therapy, a shock, to a victim.

In this embodiment, initially a determination is made as to whether a shock is advised 402. This is a typical step for AEDs. As this is a semi-automatic AED, if a shock is advised, the shock switch is activated and a user is prompted to press a shock switch 404. Referring to FIG. 1, the button the user is being prompted to push is the shock switch 110.

The user is given an amount of time to deliver a shock. The AED unit monitors to determine whether a shock has been delivered 406. In this embodiment, an initial assumption is made that if the shock is not delivered, the failure to deliver the shock is a result of a failure of the user to push the shock switch. As a result, the user is again prompted to press the shock switch 404.

As illustrated, a counter is set to track the number of times that a user is prompted to press the shock switch 110. The function of the counter is to allow the program to exit the loop of prompting the user to press the shock switch 110. As those skilled in the art will appreciate, there are many programming alternatives that can be used to exit a "do" loop, and a counter is but one of them.

If the loop is exited, a alternate shock switch is initiated, step 408. The initial presumption that the user failed to press the shock switch is replaced with the assumption that the user pressed the shock switch but it failed to initiate a shock.

It should be appreciated that the alternate shock switch could be initiated by turning the AED ON or upon the AED's decision that a shock is advised. In either of these cases, step 408 would merely be advising a user to use the alternate shock switch in lieu of the shock switch.

As with the steps associated with the shock switch, the user is prompted several times to press the alternate shock switch, step 410. If a shock is detected, step 412, normal programming is resumed. However, if after some period of time a shock is not delivered, the shock is cancelled, step 414 and normal programming is resumed.

The methods for determining whether a shock has been delivered are many and depend upon the specific hardware and software. In addition, the determination of whether a shock has been delivered could be indirect (e.g., implied), or direct. Indirect methods of determining whether a shock has been administered include, monitoring for an action associated with a shock in a portion of the circuitry that is tested by self-tests, or monitoring for a post shock event that must occur after a shock is given. Direct methods include monitoring for the actual discharge associated with the shock event.

In the illustrative AED unit, an indirect method of monitoring whether a shock as been given could involve monitoring the programming associated with the shock switch 110. As those skilled in the art will appreciate, in order to activate high voltage circuits in many cases indirect switching is employed. As used herein, indirect switching means using a switch connected to a processor such that when the switch is depressed a state of the processor is changed thereby initiating a process that culminates in the activation of the high voltage circuit and a delivery of a shock. Thus, by monitoring the state of the processor, an implication can be made as to whether a shock was delivered. This implication is made stronger if the monitored circuitry has been tested and found in working order during self-testing.

A post event could be used to indirectly monitor if a shock has been delivered. For example, the recharging of the shock circuit could be monitored. Where the AED unit programming requires the shock circuit to be recharged after discharge, the recharging would reasonably imply that a shock has been delivered.

The alternate switch could be implemented through a standalone switch, or by electronically changing the action of an existing switch. It is not a requirement that the process being implemented by the primary switch and the alternate switch be implemented in the same way.

In the case of a standalone switch, the switch would be integrated in the circuitry of the device and have the function of activating the process of the switch it is backing up. Ideally, the standalone switch should not be activated until needed, to avoid an accidental activation or user confusion. Based on the application, the switch could be of the hard turn-on type or the soft turn-on type.

Figure 5:
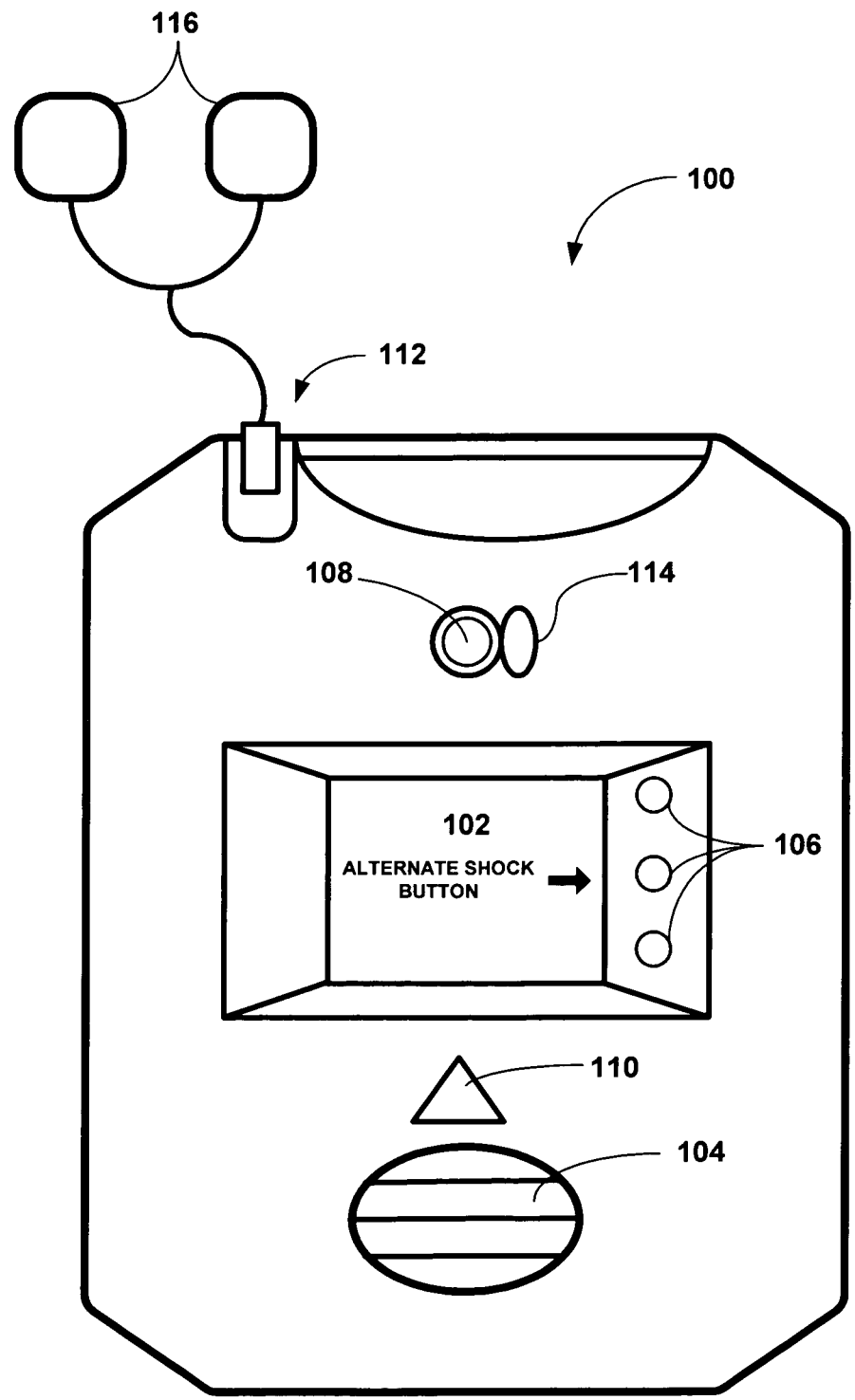
FIG. 5 is a top view of the illustrative AED depicted in FIG. 1 with an alternate shock switch indicated.

Referring to FIG. 5, changing the function of an existing switch is illustrated using the AED 100 depicted in FIG. 1. In this exemplary illustration, the user interface 106 includes three buttons. These buttons are soft buttons in that the function of each is software controllable. In other words, the current function of each button is based on the current status of the program running on the AED. For example, if the AED is in a manual test mode, the buttons may have functions associated with accomplishing that task. If the AED is in rescue mode, the buttons may have functions associated with accomplishing that task.

Thus, when the programming depicted in FIG. 4, reaches the determination of whether the shock has been delivered, step 406, the function of any one of the buttons could be set to be an alternate shock switch, step 408. Referring to FIG. 5, in this particular illustrative example the middle switch of the three switches is given this function. As explained above, the user interface 106, see FIG. 1, includes three switches. These switches are "soft switches" in that the programming running on the AED determines the switches function at any given time. As a result, a "soft switch" as used herein is a switch that has its functionality controlled by the programming and thus has at least two functions.

In addition for suitably equipped AEDs, prompts, audio or visual, could be given to user to depress the alternate shock switch. For example, where a display is present, the display could blink or the labeling associated with the button could blink. Speakers could give oral prompts.

As explained above, the alternate shock switch is generally to replace the functionality of the shock switch based on the assumption that the shock switch has failed. Thus, it is not a requirement of the invention that the shock switch has actually failed. As a result, it is possible that the alternative shock switch and the primary shock switch may be fully functional at the same time. Programming, however, my deactivate the primary shock switch upon the activation of the alternative shock switch.

The programming of AEDs is well understood in the art. In addition, the modification of the programming suggested above, is well within the capability of those skilled in the art based upon the functional description provided.

Alternative embodiments of the invention will become apparent to one of ordinary skill in the art to which the present invention pertains without departing from its spirit and scope. Thus, although this invention has been described in exemplary form with a certain degree of particularity, it should be understood that the present disclosure has been made only by way of example and that numerous changes in the details of the construction and the combination and arrangement of parts or steps may be resorted to without departing from the spirit or scope of the invention. Accordingly, the scope of the present invention is defined by the appended claims rather than the foregoing description.

What is claimed is:

1. A semi-automatic AED comprising;
   a semi-automatic AED comprising a shock switch, an alternate shock switch, and therapeutic computer circuitry capable of delivering a shock to a victim, the therapeutic computer circuitry comprising a high voltage circuit capable of delivering a shock to a victim, the shock switch and alternate shock switch permitting a shock to be delivered to a victim when at least one of the said shock switch and said alternate shock switch are pressed, and
   a program running on the therapeutic computer circuitry capable of employing the therapeutic computer circuitry to determine whether a shock should be delivered to a victim, and, where a shock should be delivered, the AED configured to activate the shock switch such that depression of the shock switch will cause a shock to be delivered to the victim, wherein the semi-automatic AED is configured to determine after activation of the shock switch whether a shock has been delivered, and, if a shock has not been delivered, the semi-automatic AED is configured to prior to cancelling the shock activating the alternate shock switch such that depression of the alternate shock switch will cause a shock to be delivered to the victim.

2. The AED of claim 1 wherein the semi-automatic AED is configured to direct a user of the AED to use the alternate shock switch when the alternate shock switch is activated.

3. The AED of claim 1 wherein the AED has soft switches and the semi-automatic AED is configured to assign the alternate shock switch to a soft switch.

* * * * *